(12) United States Patent
Dugas et al.

(10) Patent No.: US 7,772,010 B2
(45) Date of Patent: Aug. 10, 2010

(54) MIXING AND DISPENSING HOMOGENEOUS COMPOUNDS OF A REACTANT ON A SURFACE

(75) Inventors: Vincent Dugas, Meyzieu (FR); Jérôme Broutin, Lyons (FR); Eliane Souteyrand, Chambon sur Cisse (FR)

(73) Assignee: Biotray SAS, Lyon (FR)

( * ) Notice: Subject to any disclaimer, the term of this patent is extended or adjusted under 35 U.S.C. 154(b) by 201 days.

(21) Appl. No.: 11/988,640

(22) PCT Filed: Jul. 12, 2006

(86) PCT No.: PCT/EP2006/064160

§ 371 (c)(1),
(2), (4) Date: Jan. 11, 2008

(87) PCT Pub. No.: WO2007/006800

PCT Pub. Date: Jan. 18, 2007

(65) Prior Publication Data

US 2008/0223115 A1   Sep. 18, 2008

(30) Foreign Application Priority Data

Jul. 12, 2005 (FR) .................................. 05 52169

(51) Int. Cl.
*G01N 1/10* (2006.01)
*B01L 3/02* (2006.01)
*C12M 1/34* (2006.01)

(52) U.S. Cl. .................. 436/180; 436/174; 436/183; 436/178; 436/177; 422/68.1; 422/100; 422/101; 422/58; 435/287.1

(58) Field of Classification Search .................. 436/180, 436/174, 183, 178, 177; 422/68.1, 100, 101; 422/58; 435/287.1
See application file for complete search history.

(56) References Cited

U.S. PATENT DOCUMENTS 5,833,926 A * 11/1998 Wurzel et al. ................. 422/81

(Continued)

FOREIGN PATENT DOCUMENTS

EP   1 346 770   9/2003

(Continued)

OTHER PUBLICATIONS

McQuain, Mark K. et al. "Chaotic mixer improves microarray hybridization." Analytical Biochemistry 325 (Feb. 2004) 215-226.*

(Continued)

*Primary Examiner*—Yelena G Gakh
*Assistant Examiner*—Christopher A Hixson
(74) *Attorney, Agent, or Firm*—James C. Lydon

(57) ABSTRACT

A method for mixing and dispensing compounds, at least one reactant in a carrier fluid in laminar flow, and a cell for implementing the method. The cell includes a reaction chamber having a reaction surface where the reactant can be fixed, directly or indirectly, at least three fluid inlets/outlets, a fixed volume reservoir in communication with the reaction chamber and outside the reaction chamber via injection orifice (27), a fluid loop including a feeding port, an extraction port and a variable volume reservoir adapted to communicate independently with the reaction chamber via each of its inlets/outlets; device for circulating fluids in the reaction chamber and the fluid loop. The method and cell can be used to prepare homogeneous surface films, or to carry out "target-probe" identification reactions.

24 Claims, 7 Drawing Sheets

U.S. PATENT DOCUMENTS

2003/0013184 A1   1/2003  Streit et al.
2003/0096423 A1   5/2003  Ryan et al.
2004/0248125 A1  12/2004  Stremler et al.
2005/0277912 A1* 12/2005  John .................. 604/890.1

OTHER PUBLICATIONS

Stremler, Mark A. et al. "Designing for chaos: applications of chaotic advection at the microscale." Philosophical Transactions of the Royal Society 362 (Mar. 2004) 1019-1036.*

* cited by examiner

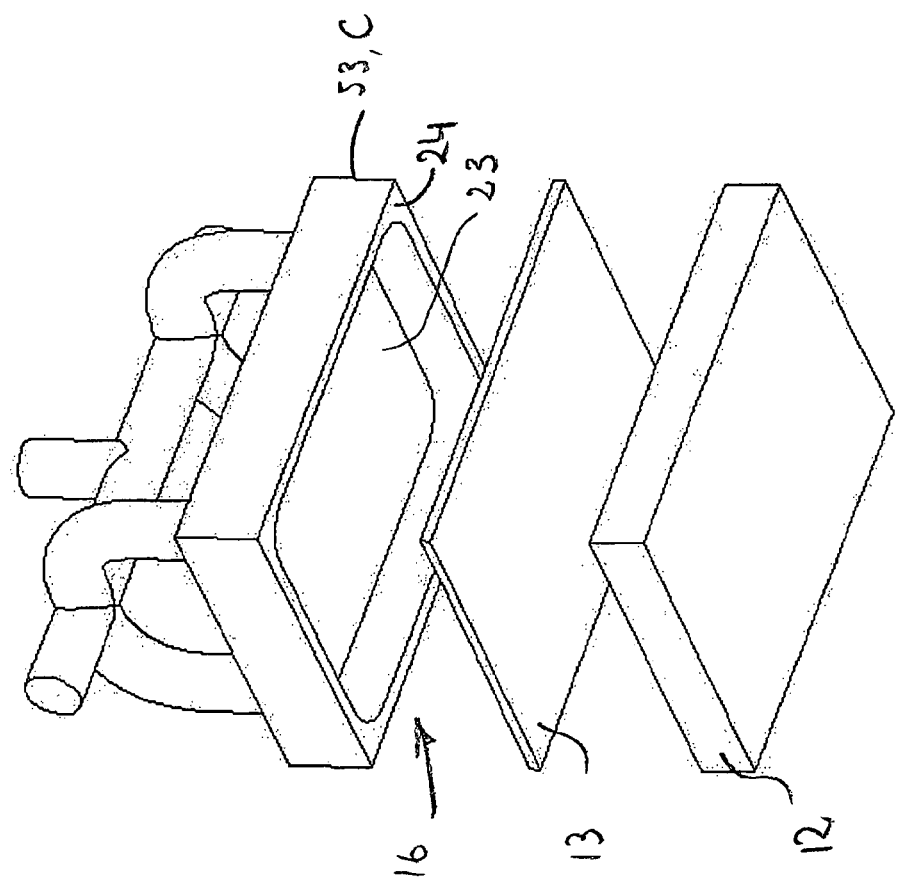
Figure 8B
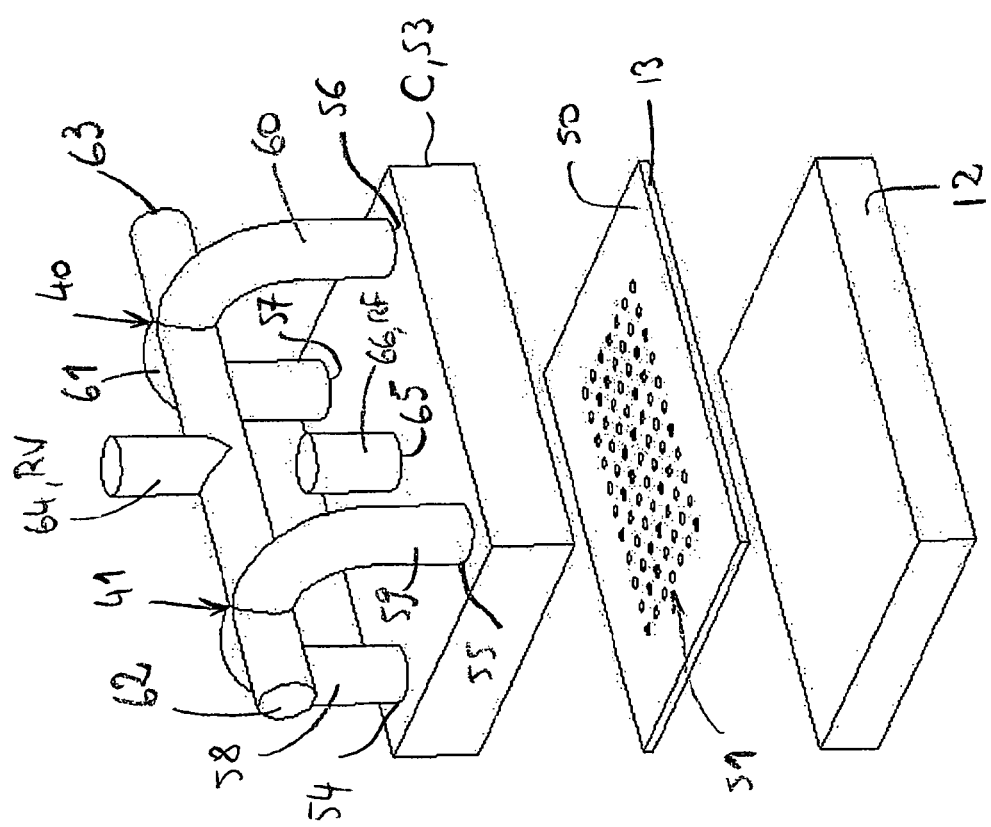
Figure 8A
Figure 8

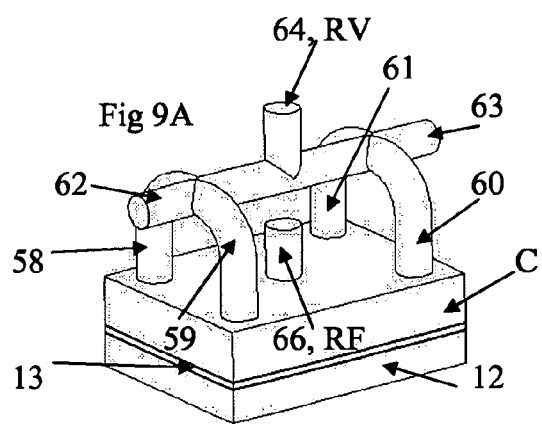
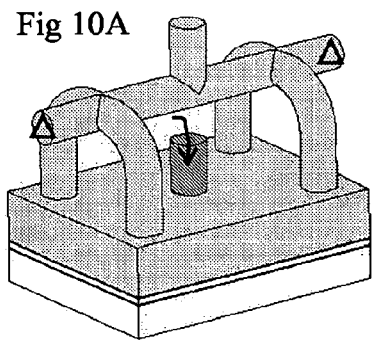
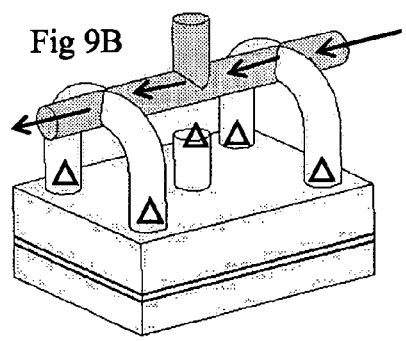
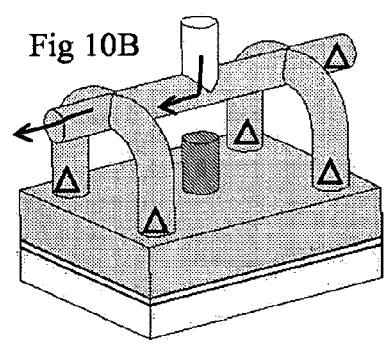
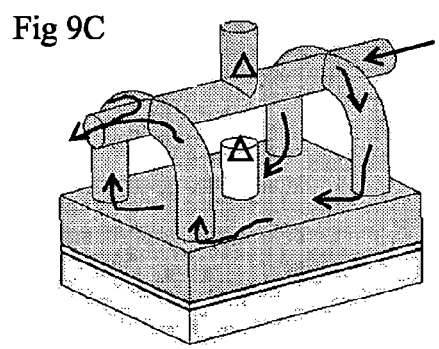
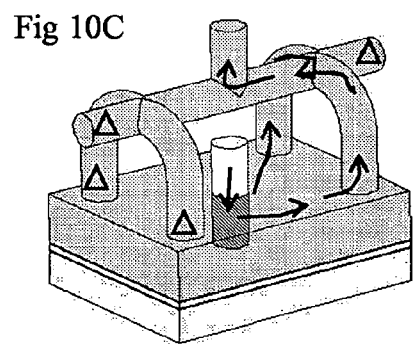
Figure 9
Figure 10

MIXING AND DISPENSING HOMOGENEOUS COMPOUNDS OF A REACTANT ON A SURFACE

FIELD OF THE INVENTION

The invention relates to the field of automatic apparatuses for the optimization of reactions on surfaces. In particular, the invention relates to a method for the homogeneous mixing and distribution, on a surface, of at least one reactant carried by a carrier fluid in laminar flow, and also to a cell for implementing this method.

The invention also relates to an automatic apparatus for carrying out biological, biochemical and chemical reactions in a homogeneous and reproducible manner on a planar or porous surface.

CONTEXT OF THE INVENTION

The fields of genomics and of post-genomics are currently in full expansion. This is closely linked to the development of new tools for high-throughput analysis. Biochips (DNA, protein, aptamers, etc.) are part of these powerful analytical tools. Biochips comprise a support on which biological or chemical molecules are localized and immobilized (from a few tens to several thousand per $cm^2$). These molecules, usually called "probes", have the ability to specifically recognize molecules in solution. Each probe has the ability to interact more or less specifically and more or less strongly with another biological or chemical molecule called "target".

Various interactions are involved. The following will be noted nonexhaustively: hybridization reactions between two complementary nucleic acid sequences (DNA chips, Fluorescence InSitu Hybridization (FISH) technique, etc.), the affinity of nucleic acids with proteins, nucleotides, drugs and organic markers (called aptamers), interactions that proteins may establish (immunoreactions, enzymatic reactions, catalytic reactions, metal binding peptide, etc.).

These techniques make it possible to screen a large amount of different molecules simultaneously. They are essential for the generation of new sources of information for biologists. In fact, the biological information making it possible to decipher molecular motifs associated with a pathology, to determine the level of gene expression in response to a stress (in particular toxicology) or else to search for polymorphisms related to genetic diseases will only be obtained using these such multiple, parallel and simultaneous screening platforms.

Another factor to be taken into account is that of the sensitivity of the tests. In fact, biological products (for example, nucleic acids, proteins, organic molecules, etc.) are extracted in minute amounts. In order to optimize the sensitivity and duration of analysis, it is sought to miniaturize the analytical devices. For example, DNA chips are known in which several hundred thousand probes are immobilized on 1 $cm^2$. A concept in full expansion in the micro- and nanotechnology field is the lab-on-chip.

A great deal of effort has thus been given over the past few years to the fabrication of these devices. However, few tests are routinely used in biological laboratories. The "young" biochip technology, for example, suffers from a lack of reliability and reproducibility. At the current time, only one example of a chip has received CE-IVD certification (AmpliChip™ CYP450, Roche). The use of chips for molecular and genetic diagnosis in a clinical laboratory, firstly, means that the results must be standardized and made reliable and, secondly, it must allow high-throughput analyses.

For this, all the steps, from the fabrication of the support to the reading of the chips and to the data processing, must be made reliable. There is an abundant literature relating to the control of processes for developing microarrays, various methods of obtaining target strands in the case of nucleic acid hybridization, and also data processing. However, few studies relate to the impact of the hybridization step on the biological results.

Two parameters appear to be important: the uniformity of the hybridization over the entire support and the automation of the process. To achieve excellent homogeneity, it is essential to give each target in solution the same probability of "seeing" all the probes attached to the support. The massive amounts of analyses required in the context of genetic diseases (for screening, for example) mean that it is necessary to have automatic tools. This aspect is important since it makes it possible to improve and guarantee good repeatability and reproducibility of the experiments, thereby reducing the multiple sources of variations.

Chips appear to be powerful analytical tools since several hundred reactions can be carried out in parallel on the same support. However, in order for all these analyses to be comparable, it is necessary for them to be subjected to the same reaction, on the scale of the probe.

In the laboratory, hybridizations on a glass slide are commonly carried out between slide and cover slip ("passive hybridization" method). The hybridization solution is therefore fixed (static) and this type of procedure is accompanied by a certain number of imperfections. In particular, this conventional hybridization method is limited by the diffusion of the targets in the hybridization buffer at the surface of the support on which the probes are immobilized (Brownian movement only).

It is found that the fact of introducing a mixture into the fluids can have a positive effect on the hybridization results. Several principles of micro-mixing associated with DNA chips have been studied. The idea is to be free of the molecular diffusion by causing a mass transfer of the DNA molecules.

A first approach is based on the migration of the charged DNA molecules under the action of an electric field (Edman et al. (1997) "Electric field directed nucleic acid hybridization on microchips" Nucleic Acid Res. 25(24): 4907-14). This method has given results 30 to 40 times superior to a passive hybridization method.

Other approaches for accelerating the hybridization make use of mass transfers by convection. A first approach is based on the generation of convection cells via acoustic waves (Liu et al. (2003) "Hybridization enhancement using cavitation microstreaming" Anal. Chem. 75(8): 1911-7). The micromixing is generated directly in the solution at the surface of the slide without the introduction of dead volumes. It has been demonstrated that this method improves the intensity of the hybridization signal and the kinetics by a factor of 5 compared with a static hybridization. The authors indicate a gain in homogeneity without giving results in terms of numbers.

The alternative consists in creating a mechanical agitation. These microfluidic systems (McQuain et al. (2004) "Chaotic mixer improves microarray hybridization" Anal Biochem. 325(2): 215-26) prove to be difficult to implement despite the simplicity of the principle. Compared with a static method, this method increases by 2- to 8-fold the hybridization effectiveness according to the probe density, the target concentration and the hybridization buffer volume. McQuain et al. (see also WO-A-03/16547) have developed a glass slide agitation system based on the principle of chaotic advection. They state that there is an improvement in the uniformity of the signal close to the uniformity of the immobilization of the probes on the support (variation coefficient of 19%) and a factor of 2 compared with a static mode.

Some of these techniques require specific supports (nanogen platform) or else expensive transducers. In addition, these systems are not integrated into automated systems, which does not make it possible to guarantee the use of small reaction volumes (comparable to systems between slide and cover slip 40-50 µl). These techniques deal more with the problem of the hybridization according to a kinetic aspect and for the most part neglect the aspects of automation and uniformity of the hybridization on the scale of the chip.

Conversely, other teams work on the access of DNA chips for mass analysis. The techniques currently used in this type of test are well plates. However, each well consumes a considerable volume of biological material and homogeneity is not ensured due to the absence of controlled agitation within the well.

A certain number of commercially available hybridization stations exist which make it possible to carry out automatic hybridizations. The volumes involved are very large (greater than 200 µl). Most of these stations perform liquid drain and fill movements with regard to the surface, which result in a laminar flow according to preferential pathways. This is accompanied by a nonuniformity of the reaction zones. McQuain et al. demonstrated the importance of creating homogeneous agitation. It is therefore important to control the manner in which the mixing is carried out.

It has been proposed to use standardized and relatively inexpensive microscope slides and to carry out mixing of the fluids by chaotic advection. The flows of liquid inside a microfluidic reaction chamber (chamber thickness less than 100 µm) follow laminar flows (very low Reynolds number). As a result, poor mixing takes place within a microchamber: the first principle consists in introducing a temporal flow variation. This is carried out by injecting the fluid at various sites periodically over time. Furthermore, in this type of periodic two-dimensional flow over time, certain regions of the fluid may resist the appearance of chaos. The introduction of a three-dimensionality of the flow, at the level of the injections, then makes it possible to eliminate these dead zones and to promote mixing over the entire surface of the slide. Simulations show that, by means of this method of mixing by chaotic advection, the target diffusion layer is reduced, which makes it possible to miniaturize the device and to apply it to diagnostic chips (biochips), in the context of a high-throughput detection.

OBJECTIVES OF THE INVENTION

The objective of the invention is to overcome the deficiencies of the devices of the prior art. In particular, it is a question of making the hybridization technique reliable, and more generally of making reliable the homogeneous mixing and distribution, on a surface, of at least one reactant carried by a carrier fluid. An objective of the invention is to develop an automatic high-throughput tool for this purpose.

Another objective is to propose a method for the homogeneous mixing and distribution, on a surface, of at least one reactant carried by a carrier fluid, which uses the phenomenon of chaotic advection generated in a laminar flow.

Another objective of the invention is to propose an automatic tool for depositing a chemical, biochemical or alternatively polymer coating, on a planar or porous surface, the thickness and homogeneity of which coating are reproducibly controlled.

An objective of the invention is to develop a method for the purpose of improving the homogeneity and the reproducibility of the chemical, biochemical and biological reaction over the whole of a reaction surface.

Another objective is to develop a cell for the homogeneous mixing and distribution, on a surface, of at least one reactant carried by a carrier fluid, in which the variability of the reaction between two points of the reaction surface is reduced.

An additional objective of the invention is to provide a method and a device that can be used in particular in the case of diagnosis—"biochips"—the fabrication and the use of which are relatively inexpensive.

Yet another objective of the invention is to propose a method that is reversible, in the sense that it may be possible to separate the reactants from the reaction surface.

The specifications of an automatic tool imply:
working with as small a volume of liquid as possible: for a unit surface, the volume of liquid is determined by the thickness of liquid with regard to the surface;
agitating the reactants in solution in order to improve the distribution of these reactants with respect to the surface, so as to obtain a homogeneous concentration on the surface;
creating a homogeneous circulation of the liquid on the surface, so as to prevent the appearance of "dead" zones;
controlling the reaction temperature;
automatically conveying several liquids;
automatically emptying the device;
being able to directly inject reactants of any type into the reaction device at any moment.

Another objective is to propose an analytical apparatus for detecting the state of advancement of the reaction, in order to optimize the duration of the reaction, both in the case of a target-probe recognition reaction and in the case of the formation of a coating, on a reaction surface.

An additional objective of the invention is to propose an apparatus for analyzing a sample, for example a biological sample. Another objective is to provide an apparatus for controlling the quality of a coating on a reaction surface.

BRIEF DESCRIPTION OF THE INVENTION

It is to the inventors' credit to have developed, firstly, a method and, secondly, a cell for homogeneously mixing and distributing, on a surface, at least one reactant carried by a carrier fluid. In particular, such a cell may be integrated into various apparatuses, in particular a chemical and/or biochemical recognition apparatus of the probe-target type, or an apparatus for forming a homogeneous film on a surface, themselves capable of comprising means for detecting the advancement of the reactions.

In order to set up this technology, the inventors have produced a fluidic system equipped with an automated hybridization chamber which makes it possible to carry out a method based on the principle of chaotic advection within the chamber.

Thus, the invention, as defined in the claims, relates firstly to a method for the homogeneous mixing and distribution, on a surface, of at least one reactant carried by a carrier fluid in laminar flow, comprising the following essential steps:
a) a reaction chamber is provided, which chamber has:
at least one reaction surface on which the reactant is capable of being fixed, directly or indirectly, optionally reversibly,
at least three fluid inlets/outlets, and
at least one reservoir, the volume of which is fixed, the fixed-volume reservoir being able to communicate, firstly, with the reaction chamber and, secondly, with the outside of the reaction chamber via an injection orifice;

b) optionally, the injection orifice of the fixed-volume reservoirs is hermetically closed or kept hermetically closed and then at least one fluid other than the carrier fluid containing the reactant is introduced into the reaction chamber via at least one inlet/outlet of the reaction chamber;

c) the carrier fluid containing the reactant is injected into at least one of the fixed-volume reservoirs;

d) the carrier fluid containing the reactant is circulated between the fixed-volume reservoir, the reaction chamber and a variable-volume reservoir able to communicate independently with the reaction chamber via each of the inlets/outlets of the reaction chamber;

e) step d) is repeated by successively selecting the various inlets/outlets;

f) optionally, steps b) and/or c) and/or d) and/or e) are repeated.

Advantageously, for the implementation of this method, the inventors have developed a cell for homogeneously mixing and distributing, on a surface, at least one reactant carried by a carrier fluid in laminar flow, comprising:

a reaction chamber which has:
  at least one reaction surface on which the reactant is capable of being fixed, directly or indirectly, optionally reversibly,
  at least three fluid inlets/outlets, and
  at least one reservoir, the volume of which is fixed, the fixed-volume reservoir being able to communicate, firstly, with the reaction chamber and, secondly, with the outside of the reaction chamber via an injection orifice equipped with hermetic closure means, a fluid loop comprising at least one feed port, at least one extraction port and at least one reservoir, the volume of which is variable, the variable-volume reservoir being able to communicate independently with the reaction chamber via each of the inlets/outlets;

means for circulating the fluids in the reaction chamber and in the fluid loop.

The method and the cell according to the invention satisfy the major requirements of the specifications mentioned above. In fact, they make it possible to develop mixing by chaotic advection within the film of carrier liquid in contact with the reaction surface.

Thus, the carrier liquid, and therefore the reactants that it carries, are distributed homogeneously over the entire reaction surface. In other words, all the points of the reaction surface are equivalent: no preferential flows of carrier fluid exist on the reaction surface.

For example, in the case of a probe-target recognition reaction (for example, by hybridization), each target has the same probability of seeing the probes immobilized on the reaction surface. In the case of the formation of a coating, the reactants intended to form the coating are distributed homogeneously over the entire reaction surface to be coated.

BRIEF DESCRIPTION OF THE FIGURES

FIG. 8 represents a perspective view of the scheme of the principle of the device.

FIG. 9 illustrates the filling of the fluid loop (9A: empty loop; 9B and 9C: priming of the fluid loop).

FIG. 10 illustrates the injection of a biological sample (10A: injection; 10B: evacuation of the excess fluid; 10C: transfer of the sample into the reaction chamber).

In FIGS. 9, 10 and 11, the arrows indicate the direction of circulation of the fluids and the symbol A indicates that the corresponding valve is blocking.

DETAILED DESCRIPTION OF THE INVENTION

The invention will now be described with reference to the figures mentioned above, essentially in the case of an automatic apparatus for hybridization on a DNA chip. Of course, other types of molecular recognition may be contemplated, for example chosen from the following probe/target pairs: DNA/DNA, DNA/RNA, RNA/RNA, PNA/DNA, PNA/RNA, PNA/protein, protein/DNA, protein/RNA, protein/protein, chemical molecule (for example, hormones, lipids, glycolipids, carbohydrate)/protein, chemical molecule/DNA, etc. (PNA: peptide nucleic acid).

Of course, this list is in no way limiting, given that the problem that the invention is intended to solve is that of the homogeneous distribution and mixing, on a reaction surface, of at least one reactant carried by a carrier fluid. In this case, reference will be made to indirect fixing of the reactant—the target—to the reaction surface, via probes immobilized on said surface.

The invention can also be applied to the deposition of reactants in order to form a homogeneous chemical, biochemical or in particular polymer film, on a reaction surface, the surface condition of which may have been modified beforehand in order to improve the deposition of the reactants. In this case, the reactant can be directly or indirectly fixed to the reaction surface, as appropriate.

The term "carrier fluid" denotes a fluid containing the reactants, i.e., in particular, the fluid which is injected into the reaction chamber via the injection orifice. Moreover, the reaction chamber generally contains an initiating fluid, for example, before the injection of the carrier fluid. As soon as the initiating fluid and the injected carrier fluid mix, the mixture is generally denoted as carrier fluid.

Figure 1:
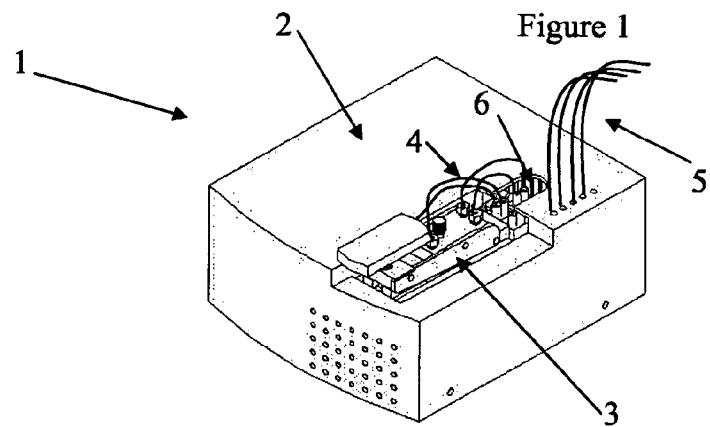
FIG. 1 represents an isometric perspective view of an automatic hybridization device.

FIG. 1 shows an isometric perspective view of an automatic hybridization apparatus 1 for hybridization on DNA chips in the microscope slide format. This apparatus comprises a cover 2, for example made of plastic, and a hybridization cell 3 into which it is possible to insert any type of microscope slide (format 1 inch×3 inch×1 mm, i.e. 26 mm×76 mm×1 mm) on which biological probes have been immobilized. The cell confines the surface to be hybridized (reaction surface on which the probes are immobilized) in a reaction chamber of small volume in which the processes relating to the hybridization will take place. This chamber is connected via the tubes 4 to a fluid loop 6 illustrated in FIG. 2. The fluid loop comprises microelectro-fluidic elements preferably located under the cover 2. These elements make it possible to carry out mixing by chaotic advection in the reaction chamber.

Advantageously, in order to control the reaction conditions, temperature regulating means make it possible to regulate the temperature of the cell, in the reaction chamber and/or in the fluid loop. This involves, for example, one or more heating elements or one or more Peltier-effect cells.

Figure 2:
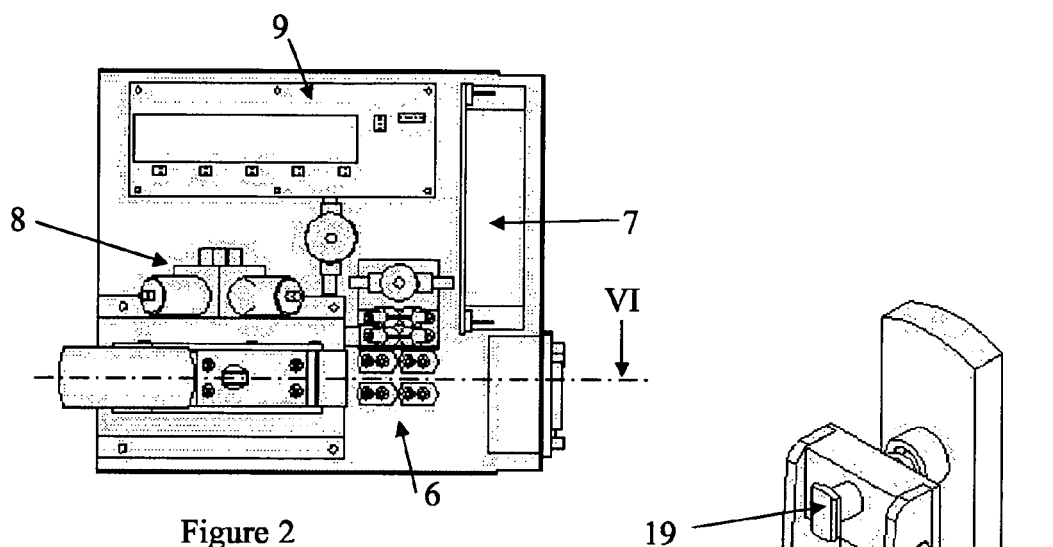
FIG. 2 represents a view of all the internal elements of the device of FIG. 1.

FIG. 2 also shows a distribution system 8 which makes it possible to distribute various solutions in the fluid loop 6 in order to carry out, for example, prehybridizations, hybridizations and/or washes. The solutions are conveyed to the distribution system 8 via the tubes 5.

The electrofluidic elements of the fluid loop and the distribution system are preferably controlled by power boards 9 protected by the cover. The temperature regulating means and also the power boards 9 are supplied by a power supply 7 under the cover which converts the alternating current of the mains supply to a 24V direct current (where appropriate).

Advantageously, the power boards and the temperature regulating means are controlled by an electronic board which has digital and analog inputs and outputs. This board is mounted on a PCI port for computers. Software controls the board which sends the information to the apparatus 1 via a cable connected to a communication port. Of course, other types of communication ports can be contemplated.

As indicated above, the invention relates to a cell 3 for homogeneously mixing and distributing, on a surface 13, at least one reactant carried by a carrier fluid in laminar flow, comprising:

a reaction chamber 16 which has:
   at least one reaction surface 13 on which the reactant is capable of being fixed, directly or indirectly, optionally reversibly,
   at least three fluid inlets/outlets 25, 26, and
   at least one reservoir, the volume of which is fixed, the fixed-volume reservoir RF being able to communicate, firstly, with the reaction chamber 16 and, secondly, with the outside of the reaction chamber via an injection orifice 27 provided with hermetic closure means 28,
a fluid loop 7 comprising at least one feed port 63, at least one extraction port 62 and at least one reservoir RV, the volume of which is variable, the variable-volume reservoir RV being able to communicate independently with the reaction chamber via each of the inlets/outlets 25, 26;
means for circulating the fluids in the reaction chamber and in the fluid loop.

Advantageously, as will be specified during the description of the method according to the invention, the volume of the fixed-volume reservoir(s) RF is greater than or equal to the maximum volume of the variable-volume reservoir RV.

Preferably, the inlets/outlets 25, 26 of the reaction chamber 16 are arranged regularly on the periphery of the reaction chamber. This makes it possible in particular to improve the homogeneity of the mixing and of the distribution of the carrier fluid along the reaction surface.

According to a preferred embodiment illustrated in FIGS. 3 to 6, the reaction chamber 16 is delimited at the top by a cover C provided with said inlets/outlets 25, 26, at the bottom by said reaction surface 13 and laterally by a leaktight seal 22. Advantageously, the lower face of the cover C comprises a peripheral groove 21 in which a leaktight O-ring seal 22 is housed.

Preferably, the reaction surface is the upper surface of a fitted part, for example a microscope slide, the cell also comprising means for positioning the fitted part relative to the cover C.

Figure 4:
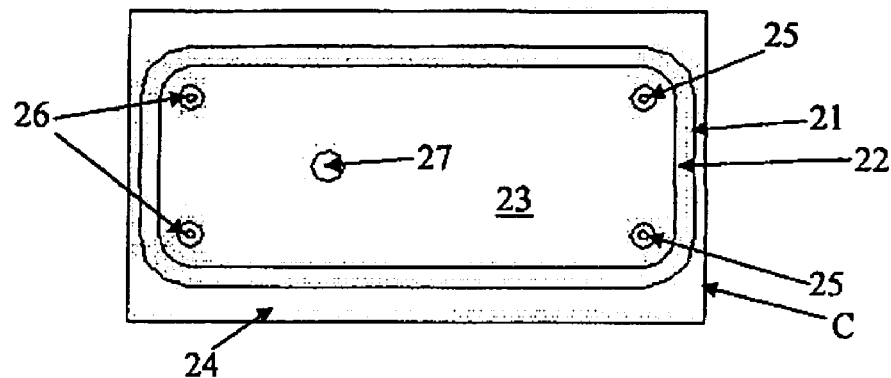
FIG. 4 represents the cover of the hybridization chamber seen from below.
Figure 5:
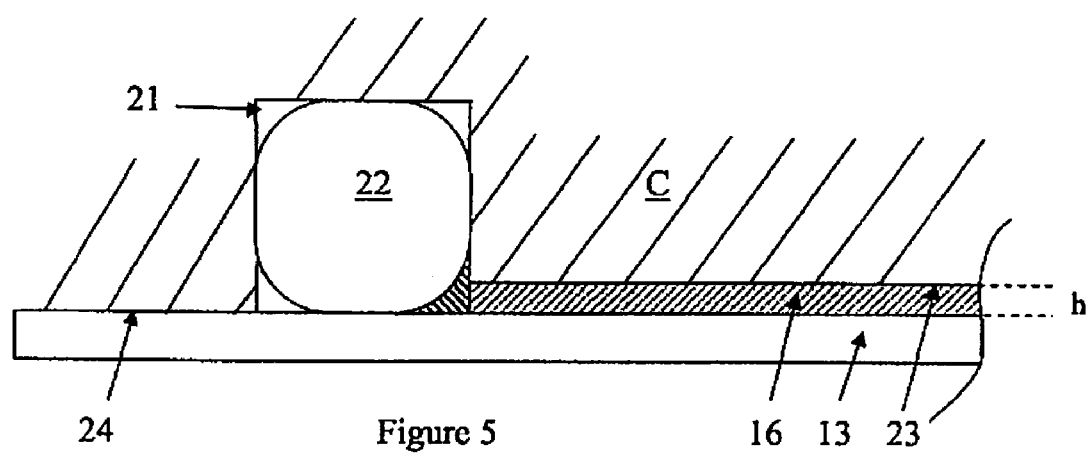
FIG. 5 represents a sectional view of the chamber applied on a microscope slide, along line V of FIG. 4.
Figure 6:
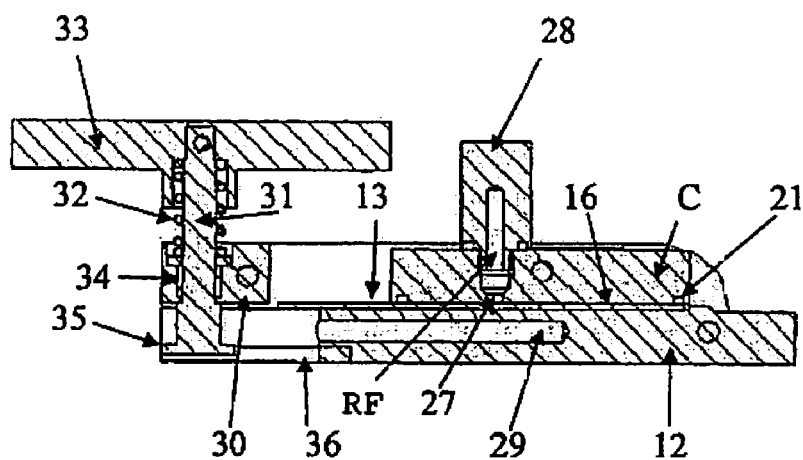
FIG. 6 represents a sectional view of the hybridization cell of the device, along line VI of FIG. 2.

FIG. 4 shows a front view of a cover C which constitutes the upper part of the reaction chamber 16. The cover C comprises a rectangular groove 21 in which an EPDM O-ring seal 22 is housed. The groove 21 delimits a rectangular inner surface 23 (in this case, 50 µm deep) which represents the top of the reaction chamber 16. When the cover C is applied to the microscope slide 13 as shown in FIG. 6, the outer surface 24 of the cover, delimited by the groove 21, is pushed against the microscope slide 13. Thus, irrespective of the thickness of the slide 13, the height (h) of the chamber 16 does not vary. When the surface 24 is pushed against the slide 13, the O-ring seal is squashed into the groove 21. This makes it possible to ensure the leaktightness of the chamber 16. In this example, the chamber comprises four inlets/outlets 25, 26 located at the four corners of the chamber. These inlets/outlets make it possible to circulate the carrier fluid and the reactants between the fixed-volume reservoir RF and the variable-volume reservoir RV, along the reaction surface. In addition, these inlets/outlets are connected to at least one feed port and at least one extraction port, which allow the injection and the extraction of the reactant solutions, washing solutions and decontaminating solutions in the device. An injection orifice 27 makes it possible to inject the biological material into the reaction chamber, during a step when the device is functioning, from the outside. This injection orifice 27 communicates with a fixed-volume reservoir RF. A stopper 28 (FIG. 6) makes it possible to hermetically close the fixed-volume reservoir RF with respect to the outside, in particular for the phases of emptying and filling the reaction chamber 16.

Figure 3:
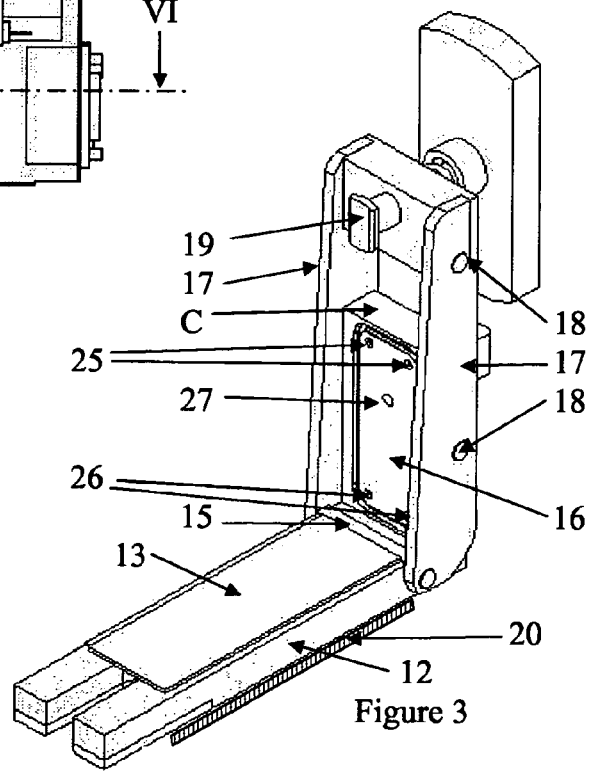
FIG. 3 represents an isometric perspective view of the open hybridization cell of the device of FIG. 1.

FIG. 3 shows a detailed isometric view of the cell 3 when it is open. The cell comprises a microscope slide support 12, for example made of fortal, on which is placed a microscope slide 13 provided with a microarray of biological probes. The slide is positioned in the horizontal plane by virtue of two abutment strips 14 and 15 machined on the support 12. The cell comprises two levers 17 connected to the support 12 via a common shaft 18 which ensures a pivot connection between the levers 17 and the support 12. The cover C is connected to the levers 17 via a shaft 18. This mechanism makes it possible to apply the cover C reproducibly to the microscope slide with a uniformly distributed force. Thus, this reduces the risks of the support breaking and this guarantees excellent leaktightness. A locking system 19 at the end of the levers 17 makes it possible to lock the system reproducibly with a sufficient force. A heating element 20 of the thermofoil type is bonded to the support 12 and makes it possible to control the hybridization temperature.

FIG. 6 shows a sectional view of the cell according to the invention. The bore 29 in the support 12 accepts a probe which makes it possible to measure the temperature of the reaction chamber 16 in proximity to the reaction surface 13, in order to be able to regulate the temperature as well as possible.

FIG. 6 makes it possible to observe the locking system 19. The shaft 31 slides in the part 30 via a polymer bushing 34. The shaft 31 is kept in place on the part 30 by virtue of the force of a spring 32 prestressed by the handle 33. To lock the cell, it is necessary to exert a force on the handle 33 so as to slide the shaft 31 into the part 30 and it is then necessary to turn the handle 33 through 90° (for example) in order to turn the shaft 31 through the same angle. The lug 35 pushes up against the part 36 which is detached as one to the support 12. Preferably, this part 36 is manufactured in a metal that is harder than the material of the support, in order to limit wearing. The system is then locked and the force of the spring 32 which keeps the system 19 locked is exerted on the cover C via the levers 17 and the shaft 18. This force is sufficient to squash the 0-ring seal 22 so that the surface 24 of the cover 16 is pressed against the microscope slide. The levers 17 make it possible to uncouple the force to be exerted on the chamber in order to allow a user to supply this force more comfortably.

Figure 7:
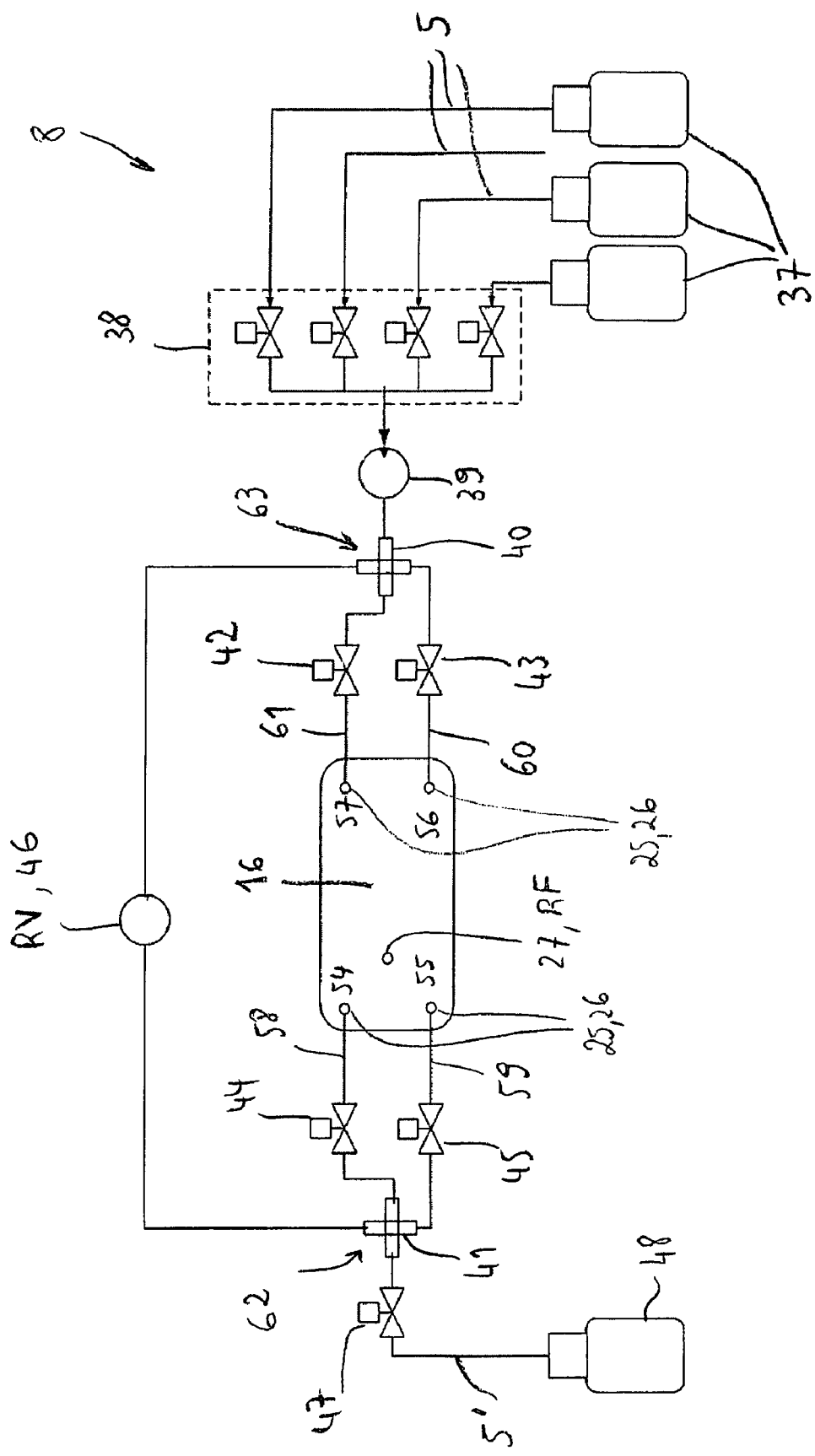
FIG. 7 represents a fluidic scheme of the device.

FIG. 7 shows the scheme of the distribution system 8 and of the fluid loop 7 connected to the reaction chamber 16. The solutions used for the hybridization operations are contained in bottles 37. The solutions are conveyed via the tubes 5 to a mixing valve 38 by virtue of a pump 39 placed downstream of the valve. It is preferably a membrane pump connected to two nonreturn valves. It may also be a solenoid valve. The mixing valve 38 makes it possible to select the solution to be used for priming the system or filling the fluid loop. The outlet of the pump 39 is connected to the fluid loop via a four-way fluid connector 40. The fluid loop comprises four valves 42, 43, 44, 45 connected respectively to the inlets/outlets 57, 56, 54, 55 of the chamber 16. The valves 42 and 43 are connected via the four-way fluid connector 40 to the outlet of the pump 39 and to the inlet of the pump 46. The valves 44 and 45 are connected to an outlet valve 47 of the loop and to the outlet of the pump 46 via the four-way fluid connector 41. A waste container 48 is placed downstream of the outlet valve 47 of the loop in order to recover the solutions used via a tube 5'.

Advantageously, the pump 46 is in the form of a solenoid valve of variable volume, which constitutes the variable-volume reservoir RV.

For the phases of filling the fluid loop including the chamber 16, the solution is selected by virtue of the mixing valve 38, and the pump 39 conveys the solution to the loop inlet. The valves 42, 43, 44 and 45 are then closed and the pump 46 and the valve 47 are opened. The pump 39 then circulates the solution toward the waste container 48. A first part of the fluid loop is filled. In order to fill the other part, the pump 46 must be closed and the valves 42, 43, 44, 45 and 47 must be opened, the pump 39 then circulates the solution toward the waste container, causing the solution to enter the chamber 16 via the inlets/outlets 57, 56 and causing the solution to exit via the inlets/outlets 54, 55. In order to fill the second part of the loop, the injection orifice of the chamber must be closed because the solution is pushed by the pump 39. Similarly, the fluid loop can be emptied by selecting air instead of a solution.

For the mixing phases, the pump 39 is closed, and the valve 47 is also closed. On the other hand, the injection orifice 27 is open or optionally closed. The mixing is carried out by a series of fluid circulation phases. In a first half of the phase, the valve 43 is open and the valves 44, 45 and 42 are closed. In the high state, the pump 46 draws up the solution via its inlet and extracts the solution from the chamber 16 via the inlet/outlet associated with the valve 43, which is open, while the other valves 44, 45 and 42 are closed. The chamber is always full because the volume of solution extracted is compensated for by the volume of solution contained in the fixed-volume reservoir RF which communicates with the injection orifice 27.

Then, in the second half of the phase, the valve 44 is open, and the valves 42, 43 and 45 are closed. The pump goes from the high state to the low state. In the low state, the pump pushes the part of the solution drawn up in the high state and injects the solution into the chamber 16 via the inlet/outlet associated with valve 44, which is open, while the other valves 42, 43 and 45 are closed. A part of the volume of the chamber equal to the volume displaced by the pump 46 is injected into the fixed volume reservoir, via the injection orifice.

The volume displaced by the pump 46 does not exceed the volume of the injection orifice so that, during the high state, no air is injected into the chamber and therefore into the loop. In fact, this can bring about head losses and poor mixing. In addition, this prevents, during the low state, the solution which fills the chamber from leaving the chamber via the injection orifice.

The pump 46 will perform a series of pulses characterized by a high state and a low state, during which the inlet/outlet connected to the pump 46 during the passage from the high state to the low state of the pump 46 and then from the low state to the high state, will change from one phase to the next. Consequently, the variable-volume reservoir can communicate with the reaction chamber independently via each of the inlets/outlets.

During the mixing, it is possible to inject biological material into the injection orifice 27 provided that there is no overspill in the low state.

Furthermore, the injection orifice operates as a bubble trap. In fact, the solutions commonly used for hybridization contain surfactants which make it very difficult to inject them without bubbles. Given that the injection orifice is released, the bubbles which enter therein are not reinjected into the chamber.

According to an advantageous characteristic of the invention, the cell is provided with means for detecting the reactants fixed to the reaction surface. For example, in the case of a nucleic acid hybridization, said means may be a fluorescence scanner.

More generally, it is possible to contemplate any type of sensor capable of detecting the presence of reactants at a given position on the reaction surface. The sensor is connected to an image analyzing device, for example, in order to determine the positions on the reaction surface where a reactant has effectively been fixed. In the case of microarrays, where a probe-target recognition is involved, the characteristics of the probes are known, which makes it possible to deduce the characteristics of the targets—the reactants fixed—and therefore, ultimately, those of the sample analyzed.

Moreover, according to the experimental conditions and the type of sensor, the analysis may be qualitative (presence or absence of a target), quantitative (amount of target present, correlated for example to a coloration or fluorescence intensity), or semi-quantitative (quantitative above a certain level of detection, and qualitative below this level of detection).

It is thus possible to have a dynamic analysis tool. For example, the hybridization reactions, or more generally the probe-target recognition reactions, are carried out by repeating phases of mixing and distributing the carrier fluid on the reaction surface, and the fixing of targets to the reaction surface is simultaneously detected using an appropriate sensor. Then, when it is determined that the situation between two detections/analyses has no longer changed for a predetermined number of cycles, i.e. no new recognition reaction has been detected, it may be considered that the analysis is complete. This makes it possible to reduce the duration of the analyses, since the mixing cycle number is not arbitrarily fixed, but depends on the situation effectively measured.

The analysis may also relate to the homogeneity of a coating. It is possible, for example, to measure the coloration of the reaction surface after having deposited a chemical, biochemical and/or polymeric film. It is also possible to contemplate measuring the variations in the intensity of a light beam passing through the film and the support. If the variability of the intensity of this light beam is less than a predetermined threshold, it may be considered, for example, that the film is homogeneous in terms of thickness. A prior calibration will make it possible to determine the thickness of this film.

Thus, a tool is provided which makes it possible to control the quality of a coating on a support such as a microscope slide.

Consequently, the invention also relates to an apparatus for carrying out chemical and/or biochemical "target-probe" recognition reactions, comprising at least one cell in accordance with the invention, in which the reaction surface of the cell is in the form of a microarray of specific probes, prepared on a support, preferably a microscope slide. In this case, the carrier fluid contains a plurality of "target" reactants capable of reacting specifically with the probes of the microarray.

The invention also relates to an apparatus for forming a homogeneous film on a surface, comprising at least one cell in accordance with the invention.

Preferably, these apparatuses comprise a device for distributing at least one fluid in the fluid loop of the mixing and distributing cell. A distributing device, for example a manifold, makes it possible to automatically distribute the fluid(s), buffer solution, cleaning solution, rinsing solution and the like, and air, used during the operating of the apparatus. According to another characteristic of the invention, means for injecting at least one carrier fluid containing said reactant into the reaction chamber of the mixing and distributing cell, via the injection orifice of the fixed-volume reservoir, are provided. Here again there is a possibility of automation, which improves the reproducibility.

It is entirely possible to contemplate having a plurality of mixing and distributing cells in parallel and/or in series. This may be useful for carrying out several recognition reactions, or several film depositions, in parallel, or even successively on the same reaction surface.

In addition, the invention relates to an analytical apparatus comprising at least one cell in accordance with the invention and means for detecting the reactants fixed to the reaction surface. The detection means may be attached to the analytical cell, or attached to the apparatus. Thus, various types of mixing and distributing cells may be contemplated, each comprising a reaction surface and detection means suitable for certain reactants, and all compatible with the same apparatus. This may prove to be useful when the same user must be able to carry out a large variety of reactions and analyses.

On the other hand, when the reaction studied is always the same, it may be preferable to attach the detection means to the analytical apparatus rather than the mixing and distributing cell, in particular to make the analyses less expensive and more reproducible.

The invention also relates, as was described above in relation to the operating of the device according to the invention, to a method for the homogeneous mixing and distribution, on a surface, of at least one reactant carried by a carrier fluid in laminar flow. This method comprises essentially the following steps.

First of all, a reaction chamber as described above is provided. Optionally, at least one fluid other than the carrier fluid containing the reactant is introduced into the reaction chamber via at least one inlet/outlet of the reaction chamber, for example in order to initiate the method, or to fill the fluid loop.

Next, the carrier fluid containing the reactant is injected into at least one of the fixed-volume reservoirs. Thus, the carrier fluid containing the reactant will be able to circulate toward the reaction chamber, via the injection orifice. The injection orifice of the fixed-volume reservoir is then closed or left open, and then the carrier fluid containing the reactant is circulated between the fixed-volume reservoir, the reaction chamber and a variable-volume reservoir able to communicate independently with the reaction chamber via each of the inlets/outlets of the reaction chamber. This operation can be carried out by placing the variable-volume reservoir in an empty state beforehand, and then filling it from the reaction chamber via an inlet/outlet. A suction which will empty the fixed-volume reservoir is thus created. This step is then reproduced, in the opposite direction, by circulating the fluid via another inlet/outlet, which makes it possible to distribute it toward another zone of the reaction surface.

Thus, preferably, it is possible to distinguish two substeps (without the order in which they are stated being obligatory):
- a substep during which the fluid is circulated from a fixed-volume reservoir to the variable-volume reservoir via a first inlet/outlet of the reaction chamber, and
- a substep during which the fluid is circulated from a variable-volume reservoir to a fixed-volume reservoir via a second inlet/outlet of the reaction chamber that is different than the first inlet/outlet.

In other words, for each step, a pair of inlets/outlets is selected. In the first substep, the fluid circulates in one direction through one of the two inlets/outlets of the pair, and then in the second substep, the fluid circulates in the opposite direction through the other of the two inlets/outlets of the pair. These two substeps are then repeated, choosing another pair of inlets/outlets, i.e. a pair which differs from the preceding pair by one or two inlets/outlets.

The previous steps are repeated, with the various inlets/outlets being successively selected. Optionally, other samples of carrier fluid containing the reactant (or a reactant other than that/those previously used) can be injected via the injection orifice of the fixed-volume reservoir, and the steps of circulating the fluids between the fixed-volume reservoir and the variable-volume reservoir can be repeated.

In certain cases, it may be necessary to flush the gas bubbles present from the device, preferably via the injection orifice of a fixed-volume reservoir. This may be carried out by leaving the injection orifice of a fixed-volume reservoir open and carrying out the mixing, such that the gas bubbles are entrained to the fixed-volume reservoir and then evacuated. In fact, the fixed-volume reservoir constitutes a high point in the reaction chamber.

Finally, the method may comprise a final step during which the reaction chamber and/or the variable-volume reservoir and/or the fixed-volume reservoir(s) is (are) drained.

Optionally, when the reaction between the reactants and the reaction surface is reversible, the final step may comprise a step for releasing the reactants. It may also be desirable to decontaminate the reaction chamber and/or the variable-volume reservoir and/or the fixed-volume reservoir(s). These operations are carried out by circulating the appropriate fluids in the fluid loop and in the reaction chamber, in a manner similar to that used for the priming.

The method will be described in detail, with reference to the schematic FIGS. 8 to 11. FIG. 8A represents a planar reaction surface 50 which comprises a micro-array 51 where biological probes have been immobilized.

A cover 53 confines the surface 51 in a small volume, which constitutes the reaction chamber. The chamber comprises at least four ports, including: three inlets/outlets and one injection orifice. In the case illustrated in FIG. 8, four inlets/outlets 54, 55, 56, 57 are distributed regularly close to the periphery of the reaction chamber and an injection orifice 65 is located close to the barycenter of the inlets/outlets. Each inlet/outlet 54, 55, 56 or 57 is connected to a fluid conduit 58, 59, 60 or 61 comprising an on/off valve, preferably a solenoid valve. The conduits 58, 59, 60 and 61 are connected to a variable-volume reservoir 64 which operates as a blocked valve when its volume is at a minimum. The conduits, the chamber and the variable volume constitute a fluid loop which also comprises a feed port 63 directly connected to the conduits 60 and 61 and an extraction port 62 directly connected to the conduits 58 and 59. The feed port 63 and the extraction port 62 each comprise an on/off valve. The injection orifice 65 of the chamber is connected to a fixed-volume reservoir 66, the volume of which is greater than or equal to the maximum volume of the variable-volume reservoir 64. The fixed-volume reservoir is provided with a leaktight closure system.

The hybridization method consists in:
1/ filling the fluid loop with a buffer solution and bringing to temperature;
2/ injecting the biological targets;
3/ extracting from the fluid loop a part of the buffer solution having the same volume as the volume of liquid injected so as not to dilute the solution too much;
4/ carrying out mixing in order to homogeneously distribute the biological targets on the micro-array of probes 51.

FIG. 9 illustrates phase 1/. In a first step, starting from the system emptied (FIG. 9A), the valves of the conduits 58, 59, 60, 61 are closed, the valves of the feed port 63 and extraction port 62 are open and the variable-volume reservoir 64 is at a maximum (valve open) (FIG. 9B). The fixed-volume reservoir 66 is closed. The buffer solution is injected via the feed port 63, thereby creating a pressure difference between the inlet and the outlet (FIG. 9B). When the buffer solution reaches the extraction port 62, the process moves onto the next step.

In a second step, the valves of the conduits 58, 59, 60, 61 are open, the valves of the feed port 63 and extraction port 62 are open and the variable-volume reservoir 64 is at a minimum (=valve closed). The fixed-volume reservoir 66 remains closed. The injection of buffer solution via the feed port is continued, and the solution passes into the chamber via the conduits 60 and 61, fills the chamber and then leaves again via the conduits 58 and 59 to the extraction port (FIG. 9C).

The fluid loop is completely filled. During this phase, the system brings the temperature to that which corresponds to the temperature required for the targets to fix to the probes.

It is possible to reverse the two steps, and also to carry them out at the same time.

FIG. 10 illustrates the phases 2/ and 3/. First of all, the valves of the feed port 63 and extraction port 62 are closed. All the other valves are open, the variable-volume reservoir 64 is at a maximum (valve open) and the fixed-volume reservoir 66 is opened. The biological targets (carrier liquid containing reactants) are injected into the fixed-volume reservoir 66. The volume injected fills the reservoir without it overflowing (FIG. 10A).

In order to carry out the mixing, it is necessary to empty the fixed-volume reservoir 66. It is therefore necessary to extract from the fluid loop the volume of buffer solution corresponding to the volume injected into the fixed-volume reservoir, without extracting the biological material. To do this, the extraction is carried out in a series of pairs of steps comprising at least one pair of phases (FIGS. 10B and 10C) in the case where the volume injected is equal to the maximum of the variable volume.

To this effect, in the next step (FIG. 10B), all the valves are closed, with the exception of the valve of the extraction port 62. The variable-volume reservoir decreases to the minimum and a volume of solution equivalent to the maximum volume of the variable volume is extracted from the loop.

The valve of the extraction port 62 then becomes closed and the valves of the conduits 60 and 61 are open. The variable-volume reservoir 64 increases to the maximum. An equivalent volume is extracted from the fixed-volume reservoir 66 (FIG. 10C).

Figure 11:
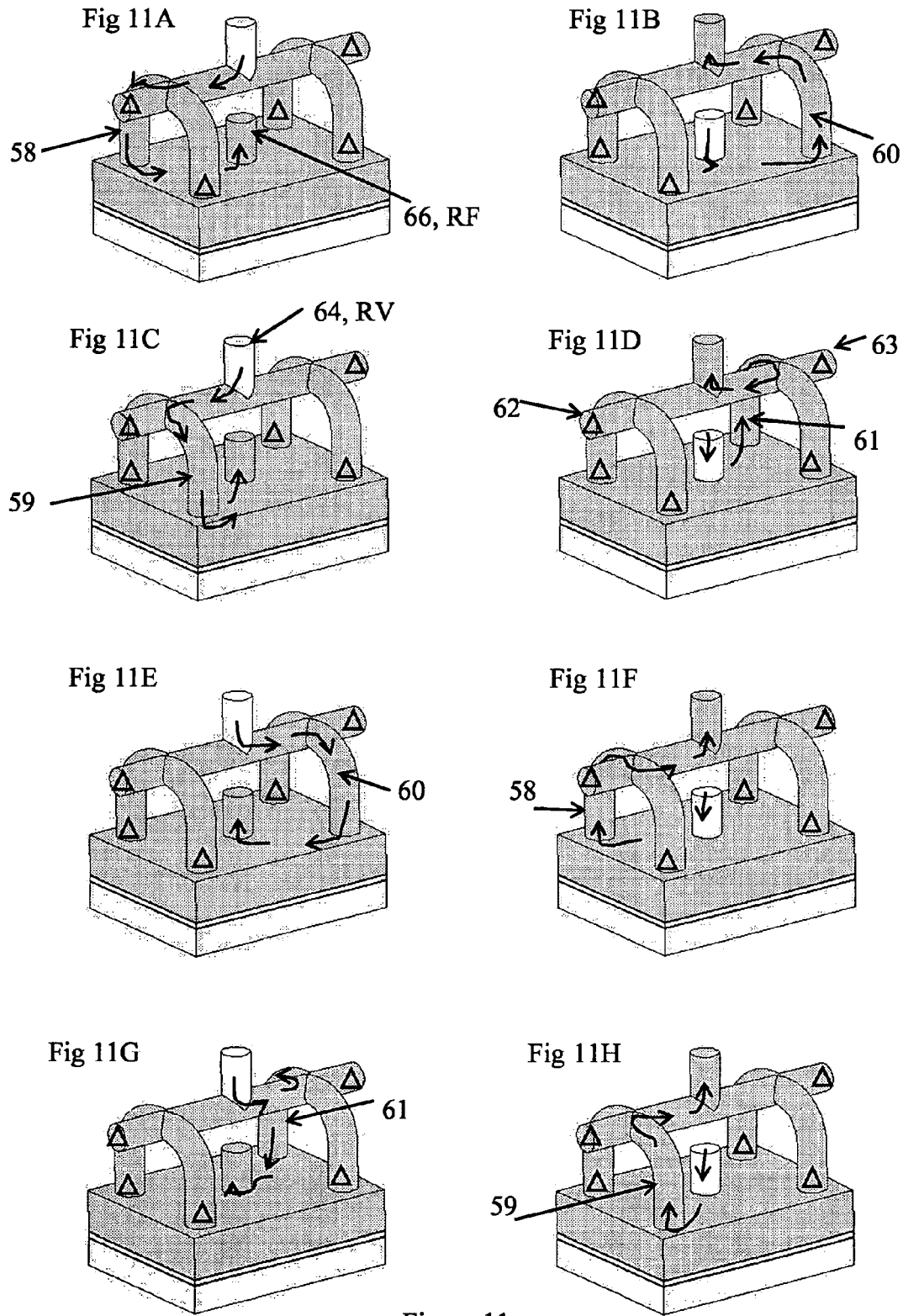
FIG. 11 illustrates several possible successive steps of the mixing phase.

FIG. 11 illustrates the mixing phase 4/. The fluid loop is filled with buffer solution and contains the biological targets. The mixing phase consists in distributing the biological targets on the microarray of probes 51, in a chaotic manner. Whatever the flow induced in the chamber, it will be laminar and there is a risk that the biological targets will take the same path and encounter the same probes. In order for the recognition between the targets and the probes to be more homogeneous over the surface, a chaotic flow is created from the several laminar flows, which thus multiplies the chances of "match" between the targets and the probes.

The mixing is a succession of 4 steps which are repeated sequentially throughout the duration of the reaction. Each step comprises 2 substeps:
 a first substep during which the variable-volume reservoir decreases to the minimum. One of the four inlets/outlets is open and the others are closed. A volume equivalent to the maximum volume of the variable-volume reservoir is injected into the chamber and the excess is injected into the fixed-volume reservoir 66. The flow therefore goes from the variable-volume reservoir to the fixed-volume reservoir;
 a second substep during which the variable-volume reservoir increases to the maximum, an inlet/outlet different than the previously open inlet/outlet becomes open, whereas the others are closed. For example, the inlet/outlet which becomes open is that which is opposite the inlet/outlet previously open. A volume equivalent to the maximum volume of the variable-volume reservoir is extracted from the chamber and the same volume is therefore extracted from the fixed-volume reservoir to the chamber. The flow goes from the fixed-volume reservoir to the variable-volume reservoir.

Thus, for example:
Phase 1: the solution is injected via the inlet 54 (FIG. 11A) and the solution is extracted via the outlet 56 (FIG. 11B). Phase 2: the solution is injected via the inlet 55 (FIG. 1C) and the solution is extracted via the outlet 57 (FIG. 1D). Phase 3: the solution is injected via the inlet 56 (FIG. 11E) and the solution is extracted via the outlet 54 (FIG. 11F). Phase 4: the solution is injected via the inlet 57 (FIG. 11G) and the solution is extracted via the outlet 55 (FIG. 11H).

It is of course entirely possible to contemplate carrying out the injections and extractions randomly, or else extracting the fluid simultaneously via a pair of inlets/outlets, and then reinjecting it into the reaction chamber via another pair of inlets/outlets.

EXAMPLES

A—Materials and Methods

Biological Material

The company Sequentia (Evry, France) supplied the HPLC-purified oligonucleotides. Each probe was synthesized with an amino group ($-CH_2-)_6-NH_2$ attached to its 5' end.

A 25-oligomeric control probe for verifying immobilization, labeled with Cy3™, and two 12-oligomeric probes (allele a and allele b) which contained a single central point mutation (G in place of A), were used in this experiment.

84-oligomeric single-stranded synthetic DNA targets labeled with Cy3™, with a sequence complementary to the two 12-oligomeric probes, were used in this experiment. The targets were diluted in a 6×SSC/0.1% SDS hybridization solution.

Biochip Fabrication

Microarrays were fabricated on a RosaSlide substrate (RosaTech, France) using 25 µM of probes diluted in a 10× PBS solution. The RosaTech 192-point multimicro-projection apparatus was used to deposit approximately 5 nl of probe solution at each point, without contact or cross contamination. The surface of the substrate was inactivated using the RosaBlock solution (RosaTech, France). This step minimizes the adsorption during the hybridization. The microarrays were washed using a 1% SDS solution for 30 minutes at 80° C., and then rinsed for 30 minutes with hot water at 80° C. This treatment, which ensures the reproducibility between microarrays, eliminates the oligonucleotide probes not covalently bound to the substrate.

285 deposits were arranged uniformly with a gap of 1 mm on the 42×15 mm$^2$ surface of the substrate. The microarray consists of identical clusters formed by a checkered design of deposits of the two alleles. Each cluster is separated by the fluorescence-labeled verification control probe.

The Hybridization Station According to the Invention

The TrayMix micromixer is an automatic active mixing and hybridization station which is compatible with a standard microscope slide. The reaction chamber has the following dimensions: 18.8 mm×49 mm×50 µm (width×length×height), and is sealed by means of a circular seal. The automatic fluidic system of mixing by chaotic advection is shown schematically in FIG. 7.

The chaotic mixing is created by means of periodic intersecting flows produced by means of microvalves inside the reaction chamber. The feed and extraction ports and the inlets/outlets allow various solutions (hybridization, washing, decontaminating solutions) to be injected into the chamber and liquids to be extracted, in particular to the waste container. A computer controls the operation of the device via a user software interface. The user simply injects the targets directly into the reaction chamber through the injection orifice. The system creates mixing by chaotic advection, without any loss of precious biological sample. The total volume inside the mixing system is 500 µl. The hybridization temperature is controlled by means of a heating element which can range between 20 and 80° C.±0.5° C.

Hybridization

1—Passive Hybridization (Static)

1.1—Method Between Slide and Cover Slip (Manual)

The results obtained according to the conventional method of hybridization between slide and cover slip are used as a base threshold for the comparisons. Ideally, a small amount of target (approximately 50 µl) is placed between the surface of the slide carrying the microarray and the cover slip. The hybridization is carried out in a confined environment, under controlled relative humidity and temperature.

1.2—Micromixer without Chaotic Mixing

The slide carrying the microarray is placed in the micromixer. For the hybridization, the device mixer features are turned off and a homogeneous solution of target is introduced into the reaction chamber.

2—Passive Hybridization (Dynamic)

Two distinct hybridization protocols were used independently in order to demonstrate the advantages of the chaotic mixing inside the reaction chamber:

2.1—Automatic Hybridization with a Homogeneous Target Solution:

1. Manual insertion of the microarray into the reaction chamber.
2. Automatic bringing to temperature and automatic initializing of the system with a homogeneous target solution.
3. Automatic mixing in the reaction chamber.
4. Automatic extraction of the reactants from the reaction chamber.
5. Manual withdrawal of the microarray.
6. Automatic washing of the chamber with ultrapure water, in preparation for successive hybridizations.

2.2—Automatic Hybridization with Injection of the Target Solution into the Initialized Mixing Loop 1. Manual insertion of the microarray into the reaction chamber.
2. Automatic bringing to temperature and automatic initializing of the system with a buffer solution.
3. Manual injection of the target solution into the reaction chamber via the injection orifice.
4. Automatic mixing in the reaction chamber.
5. Automatic extraction of the reactants from the reaction chamber.
6. Manual withdrawal of the microarray.
7. Automatic washing of the chamber with ultrapure water, in preparation for successive hybridizations.

The comparison of the results obtained according to these two protocols was used to demonstrate the advantages of the chaotic mixing according to the invention. All the hybridization experiments were carried out in two hours, except the kinetics experiments.

Washing of Microarrays

All the hybridized arrays were washed for two minutes in a solution of 5×SSC and 0.1% SDS, followed by washing in a solution of 2×SSC. The microarrays were then dried by centrifugation at 1500 g for one minute before being scanned.

Scanning and Analysis of Results

The microarrays were scanned, with two PMT gains, using GeneTAC™ LS IV (Genomic Solutions Ltd, Cambridgeshire, UK) at a resolution of 10 µm for scanning the immobilized control probes and the hybridized probes (allele a and allele b) at subsaturation.

The fluorescence intensity of each point was analyzed by segmentation using the TARGET software developed by LEOM (http://leom.ec-lyon.fr/). The average signal intensity of each point was measured on the microarray. The coefficient of variation (CV) was calculated on the basis of the measurements carried out. The CV was determined from the ratio of the standard deviation of the intensity of the signals to the average intensity of the signal for the same population. This coefficient makes it possible to compare the homogeneity of hybridization over the entire surface of the substrate. The signal intensities of the Cy3™-labeled control probes for the three microarrays were used to determine the intrinsic heterogeneity of the microarrays. The overall CV of the substrate was between 0.10 and 0.15.

B—Results

Given that the volumes used in the micromixer are 10 times greater than in the method between slide and cover slip (500 µl compared with 50 µl), two series of experiments were carried out.

In a first series of experiments, a similar target concentration was used under two experimental conditions:
1. Static: between slide and cover slip (1.1) and in the micromixer with the mixing functions turned off (1.2).
2. Dynamic: micromixer with the mixing functions operating.

In the second series of experiments, the same amount of targets was used, diluted in 50 µl for the method between slide and cover slip, and in 500 µl for the methods in the micromixer.

Effect of the Chaotic Mixing on the Hybridization (Identical Concentrations)

In order to determine the impact of the active mixing, the hybridization results obtained with the micromixer with or without chaotic mixing were compared. The results show the advantages, in terms of signal intensity and homogeneity, of the dynamic hybridization compared with the static hybridization.

The fluorescence results and the CV of the hybridization between slide and cover slip serve as a reference. The high CV of this technique demonstrates the nonuniformity of the hybridization response inherent in the method between slide and cover slip. Even if the initial target solution is homogeneous, the CV for hybridization in the mixing loop without chaotic mixing is even greater (0.56).

The chaotic mixing makes it possible to reduce the CV for hybridization almost to the value of the CV intrinsic to the microarrays, irrespective of whether or not the injected solution is homogeneous.

Tests with an Identical Amount of Target

The two static and dynamic hybridization experiments were carried out with 5 pmol of target.

Figure 12:
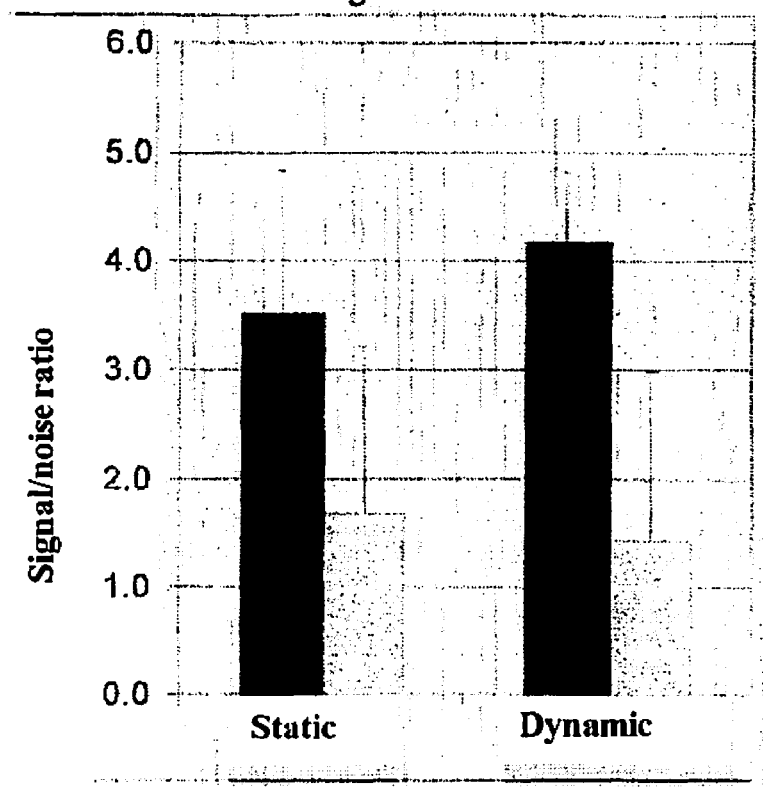
FIG. 12 is a graph representing the signal/noise ratio (SNR) for two types of probes exhibiting a single nucleotide polymorphism, and in two hybridization techniques (technique between slide and cover slip, compared with the dynamic technique of chaotic mixing according to the invention), as explained in the examples (signal/noise ratio; shown as black: allele a; shown as hatched: allele b).

Even if the target solution used with the micromixer was 10 times less concentrated than that used with the method between slide and cover slip, the micromixer made it possible to obtain results that were superior in terms of intensity and of CV. The signal/noise ratios (SNRs) for each type of probe are represented in FIG. 12.

The dynamic hybridization made it possible to increase the hybridization specificity for the detection of a single nucleotide polymorphism (SNP) by increasing the SNR for allele a (represented as black) and by reducing the SNR for allele b (represented as hatched).

Figure 13:
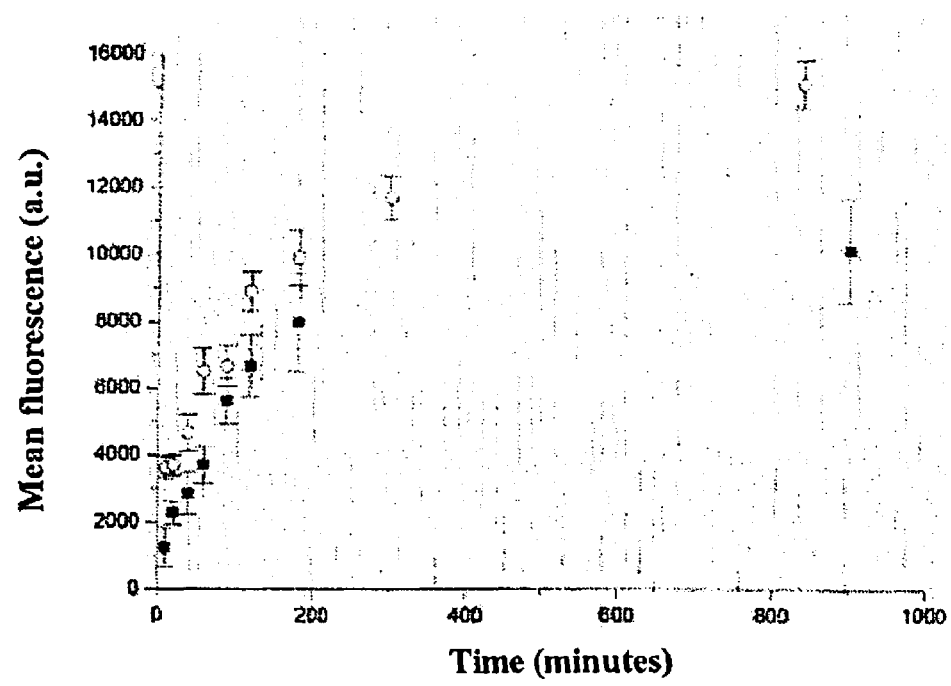
FIG. 13 illustrates the overall kinetics of hybridization for the static and dynamic hybridizations, as explained in the examples (average fluorescence [arbitrary units, a.u.] as a function of time [min]; black square: static hybridization; circle: dynamic hybridization according to the invention).

The overall kinetics of the reaction are an important parameter to be studied since the target concentrations between the two techniques are very different. FIG. 13 illustrates the overall hybridization kinetics for the static (black square) and dynamic (circle) hybridizations. The two curves are similar, which suggests that the hybridization rates are of the same order of magnitude. That said, at any moment, the signal intensity and the standard deviation are improved with the dynamic hybridization compared with the static hybridization.

With each method, the asymptotic value for hybridization is not reached. The reduction in the degree of hybridization is less pronounced with the chaotic mixing, due to the constant supply of target molecules on the reaction surface, obtained by the active mixing (target/probe ratio=50).

The chaotic mixing results in an improvement in the reaction kinetics and a rapid distribution of the targets over the entire reaction surface. After 30 minutes, the hybridization signals in the case of the active mixing are greater than those obtained in the case of the technique between slide and cover slip.

It is noted that, in less than 200 minutes of dynamic hybridization, results similar to those of an overnight hybridization between slide and cover slip are obtained. This speed, approximately four times greater for the dynamic hybridization, is a further advantage of the method according to the invention, in addition to the improvement in the homogeneity and to the increase in the signal intensity which are obtained with the dynamic hybridization.

The principal advantages of the present invention can be summarized as follows:

Uniform and homogeneous mixing without a dead zone at the reaction surface of the support to be processed (visualized by homogenization and mixing of a fluorescent label in the chamber initialized with a buffer solution).

Improvement in reaction rates, compared with the static techniques between slide and cover slip, optimization of the duration and of the number of reaction cycles.

Highly uniform biological response over the entire zone processed: the coefficient of variation of the order of magnitude of the intrinsic uniformity of the support, i.e. the intrinsic "noise" of the support.

Automation of the entire method, which results in an improvement in reproducibility.

Improvement in the specificity between two simple mutations.

Possibility at any moment of adding reactants to the reaction chamber, via the injection orifice. This is advantageous, for example, for double labeling systems (ELISA type).

Possibility of introducing into the fluid loop a heating element (>90° C.) for performing denaturations of double-stranded targets or alternatively breaking the secondary structures of targets outside the reaction chamber.

In particular, the invention finds its application:
in high-throughput screening techniques,
in biochips: DNA (microarray, fluorescence in situ hybridization (FISH), complete genome hybridization), peptides, proteins, glycoproteins, enzymes, catalysis, cells, organisms, etc.),
in catalytic reactions (selection of metal binding protein, for example), enzymatic reactions, etc.,
in chemical and electrochemical reactions.

The invention claimed is:

1. A method for the homogeneous mixing and distribution, on a surface, of at least one reactant carried by a carrier fluid in laminar flow, comprising the following essential steps:
   a) a reaction chamber is provided, which chamber has:
      at least one reaction surface on which the reactant is capable of being fixed, directly or indirectly, optionally reversibly,
      at least three fluid inlets/outlets, and
      at least one reservoir, the volume of which is fixed, the fixed-volume reservoir being able to communicate, firstly, with the reaction chamber and, secondly, with the outside of the reaction chamber via an injection orifice equipped with hermetic closure means;
   b) optionally, the injection orifice of the fixed-volume reservoirs is hermetically closed or kept hermetically closed and then at least one fluid other than the carrier fluid containing the reactant is introduced into the reaction chamber via at least one inlet/outlet of the reaction chamber;

c) the carrier fluid containing the reactant is injected into at least one of the fixed-volume reservoirs;

d) the carrier fluid containing the reactant is circulated between the fixed-volume reservoir, the reaction chamber and a variable-volume reservoir able to communicate independently with the reaction chamber via valves placed between the variable-volume reservoir and each of the inlets/outlets of the reaction chamber using a means for circulating the fluids in the reaction chamber and the fluid loop;

e) step d) is repeated by successively selecting the various inlets/outlets;

f) optionally, steps b) and/or c) and/or d) and/or e) are repeated.

2. The method as claimed in claim 1, in which steps d) and e) respectively comprise:
a substep d1) and e1) during which the fluid is circulated from a fixed-volume reservoir to the variable-volume reservoir via a first inlet/outlet of the reaction chamber, and
a substep d2) and e2) during which the fluid is circulated from a variable-volume reservoir to a fixed-volume reservoir via a second inlet/outlet of the reaction chamber that is different than the first inlet/outlet.

3. The method as claimed in claim 1, in which step b) comprises an initiating step during which an initiating fluid is introduced into the reaction chamber via at least one inlet/outlet of the reaction chamber.

4. The method as claimed in claim 1, comprising a final step during which at least one of the reaction chamber, the variable-volume reservoir and the fixed-volume reservoir(s) is (are) drained.

5. The method as claimed in claim 4, in which the final step also comprises a step of releasing the reactants, or a step of decontaminating at least one of the reaction chamber, the variable-volume reservoir and the fixed-volume reservoir(s).

6. The method as claimed in claim 1, comprising at least one step of flushing gas bubbles.

7. The method as claimed in claim 1, in which the reaction surface carries a plurality of probes grafted onto said surface, and in which said reactants are capable of reacting specifically with said probes.

8. The method as claimed in claim 1, in which the reactants are able to form a homogeneous film on the reaction surface.

9. A method of analysis, comprising the implementation of a method for homogeneous mixing and distribution on a surface as claimed in claim 1, further comprising a step of detecting the reactants fixed to the reaction surface.

10. A cell for homogeneously mixing and distributing, on a surface, at least one reactant carried by a carrier fluid in laminar flow, comprising:
a reaction chamber which has:
at least one reaction surface on which the reactant is capable of being fixed, directly or indirectly, optionally reversibly,
at least three fluid inlets/outlets, and
at least one reservoir, the volume of which is fixed, the fixed-volume reservoir being able to communicate, firstly, with the reaction chamber and, secondly, with the outside of the reaction chamber via an injection orifice equipped with hermetic closure means,
a fluid loop comprising at least one feed port, at least one extraction port and at least one reservoir, the volume of which is variable, the variable-volume reservoir being able to communicate independently with the reaction chamber via valves placed between the variable-volume reservoir and each of the inlets/outlets;
means for circulating the fluids in the reaction chamber and in the fluid loop.

11. The cell as claimed in claim 10, in which the volume of the fixed-volume reservoir(s) is greater than or equal to the maximum volume of the variable-volume reservoir.

12. The cell as claimed in claim 10, in which the inlets/outlets of the reaction chamber are arranged regularly on the periphery of the reaction chamber.

13. The cell as claimed in claim 10, in which the reaction chamber is delimited at the top by a cover provided with said inlets/outlets, at the bottom by said reaction surface and laterally by a leaktight seal.

14. The cell as claimed in claim 13, in which the lower face of the cover comprises a peripheral groove in which a leaktight O-ring seal is housed.

15. The cell as claimed in claim 13, in which the reaction surface is the upper surface of a fitted part, the cell also comprising means for positioning the fitted part relative to the cover.

16. The cell as claimed in claim 10, further comprising means for regulating the temperature in the chamber or means for regulating the temperature in the fluid loop.

17. The cell as claimed in claim 16, in which the means for regulating the temperature are in the form of at least one Peltier-effect cell.

18. The cell as claimed in claim 13, comprising means for locking the cover relative to the reaction surface.

19. The cell as claimed in claim 10, also comprising means for detecting the reactants fixed to the reaction surface.

20. A chemical or biochemical "target-probe" recognition apparatus, comprising at least one cell as claimed in claim 10, in which the reaction surface of the cell is in the form of a microarray of specific probes, prepared on a support, and in which the carrier fluid contains a plurality of "target" reactants capable of reacting specifically with the probes of the microarray.

21. An apparatus for forming a homogeneous film on a surface, comprising at least one cell as claimed in claim 10.

22. The apparatus as claimed in claim 20, comprising:
a device for distributing at least one fluid in the fluid loop of the mixing and distributing cell;
means for injecting at least one carrier fluid containing said reactant into the reaction chamber of the mixing and distributing cell.

23. The apparatus as claimed in claim 20, in which a plurality of mixing and distributing cells are placed in parallel or in series.

24. An analytical apparatus comprising an apparatus as claimed in claim 20 and means for detecting the reactants fixed to the reaction surface.

* * * * *